(12) United States Patent
Shiroff et al.

(10) Patent No.: US 7,418,298 B2
(45) Date of Patent: Aug. 26, 2008

(54) MYOCARDIAL LEAD WITH FIXATION MECHANISM

(75) Inventors: Jason Alan Shiroff, Shoreview, MN (US); Ronald W. Heil, Jr., Roseville, MN (US); Peter T. Kelley, Buffalo, MN (US); M. Sean Coe, Plymouth, MN (US); Randy W. Westlund, River Falls, WI (US); Donald F. Palme, II, Princeton, MN (US); David B. Yingling, Stillwater, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 377 days.

(21) Appl. No.: 10/971,549

(22) Filed: Oct. 22, 2004

(65) Prior Publication Data

US 2005/0113900 A1    May 26, 2005

Related U.S. Application Data

(60) Provisional application No. 60/514,037, filed on Oct. 24, 2003, provisional application No. 60/514,042, filed on Oct. 24, 2003, provisional application No. 60/514,039, filed on Oct. 24, 2003, provisional application No. 60/514,146, filed on Oct. 24, 2003, provisional application No. 60/514,038, filed on Oct. 24, 2003, provisional application No. 60/514,665, filed on Oct. 27, 2003, provisional application No. 60/514,713, filed on Oct. 27, 2003, provisional application No. 60/514,714, filed on Oct. 27, 2003.

(51) Int. Cl.
*A61N 1/05* (2006.01)

(52) U.S. Cl. ..................................... 607/126; 607/129
(58) Field of Classification Search ................. 607/126, 607/128, 125, 116, 122, 119, 123; 600/375
See application file for complete search history.

(56) References Cited

U.S. PATENT DOCUMENTS 3,244,174 A    4/1966    Wexbey et al.

(Continued)

FOREIGN PATENT DOCUMENTS

DE    2219044    11/1972

(Continued)

OTHER PUBLICATIONS

Assad et al., New Lead for In-Utero Pacing for Fetal Congenital Heart Block, Journal of Thoracic and Cardiovascular Surgery, Jul. 2003.

(Continued)

*Primary Examiner*—Carl H. Layno
*Assistant Examiner*—Natasha N Patel
(74) *Attorney, Agent, or Firm*—Faegre & Benson LLP

(57) ABSTRACT

The present invention is a myocardial lead attachment system and method for securing a distal end of a lead within the myocardium of a patient's heart. The system includes an anchor, a tether coupled at a distal end to the anchor and a lead body. The lead body has a proximal end, a distal end, and a lumen extending therethrough for receiving the tether. A fixation mechanism is at the distal end of the lead body, and is adapted to collapse to a first configuration during implantation and deploy to a second configuration after implantation.

18 Claims, 9 Drawing Sheets

U.S. PATENT DOCUMENTS

| | | | |
|---|---|---|---|
| 3,474,791 A | 10/1969 | Bentov | |
| 3,737,579 A | 6/1973 | Bolduc | |
| 4,142,530 A | 3/1979 | Wittkampf | |
| 4,161,952 A | 7/1979 | Kinney et al. | |
| 4,258,724 A | 3/1981 | Balat et al. | |
| 4,341,226 A | 7/1982 | Peters | |
| 4,355,642 A | 10/1982 | Alferness | |
| 4,378,023 A | 3/1983 | Trabucco | |
| 4,444,207 A | 4/1984 | Robicsek | |
| 4,475,560 A * | 10/1984 | Tarjan et al. | 607/128 |
| 4,628,944 A | 12/1986 | MacGregor et al. | |
| 4,633,880 A | 1/1987 | Osypka et al. | |
| 4,735,205 A | 4/1988 | Chachques et al. | |
| 4,827,940 A * | 5/1989 | Mayer et al. | 600/375 |
| 4,991,578 A | 2/1991 | Cohen | |
| 5,009,229 A | 4/1991 | Grandjean et al. | |
| 5,217,027 A | 6/1993 | Hermens | |
| 5,241,957 A | 9/1993 | Camps et al. | |
| 5,300,107 A * | 4/1994 | Stokes et al. | 607/126 |
| 5,314,463 A | 5/1994 | Camps et al. | |
| 5,318,543 A | 6/1994 | Ross et al. | |
| 5,327,909 A | 7/1994 | Kiser et al. | |
| 5,336,252 A | 8/1994 | Cohen | |
| 5,350,419 A | 9/1994 | Bendel et al. | |
| 5,385,579 A * | 1/1995 | Helland | 607/130 |
| 5,423,876 A | 6/1995 | Camps et al. | |
| 5,693,081 A | 12/1997 | Fain et al. | |
| 5,716,392 A | 2/1998 | Bourgeois et al. | |
| 5,755,767 A | 5/1998 | Doan et al. | |
| 5,807,399 A | 9/1998 | Laske et al. | |
| 5,836,994 A | 11/1998 | Bourgeois | |
| 5,871,532 A | 2/1999 | Schroeppel | |
| 6,041,258 A | 3/2000 | Cigaina et al. | |
| 6,173,206 B1 | 1/2001 | Shchervinsky | |
| 6,304,786 B1 | 10/2001 | Heil, Jr. et al. | |
| 6,360,129 B1 | 3/2002 | Ley et al. | |
| 6,360,130 B1 | 3/2002 | Duysens et al. | |
| 6,370,434 B1 | 4/2002 | Zhang et al. | |
| 6,405,091 B1 * | 6/2002 | Vachon et al. | 607/120 |
| 6,434,431 B1 | 8/2002 | Camps et al. | |
| 6,459,937 B1 | 10/2002 | Morgan et al. | |
| 6,473,654 B1 | 10/2002 | Chinn | |
| 6,491,707 B2 | 12/2002 | Makower et al. | |
| 6,510,332 B1 | 1/2003 | Greenstein | |
| 6,512,958 B1 | 1/2003 | Swoyer et al. | |
| 6,567,704 B2 | 5/2003 | Sundquist et al. | |
| 6,613,062 B1 | 9/2003 | Leckrone et al. | |
| 6,626,919 B1 | 9/2003 | Swanstrom | |
| 6,671,553 B1 * | 12/2003 | Helland et al. | 607/37 |
| 6,671,561 B1 | 12/2003 | Moaddeb | |
| 6,842,648 B2 | 1/2005 | Partridge et al. | |
| 6,941,174 B2 | 9/2005 | Shchervinsky | |
| 2001/0000349 A1 | 4/2001 | Coe et al. | |
| 2001/0039436 A1 | 11/2001 | Frazier et al. | |
| 2002/0013571 A1 | 1/2002 | Goldfarb et al. | |
| 2002/0072787 A1 * | 6/2002 | Partridge et al. | 607/122 |
| 2002/0077685 A1 | 6/2002 | Sundquist et al. | |
| 2002/0123785 A1 | 9/2002 | Zhang et al. | |
| 2002/0183818 A1 | 12/2002 | Williams et al. | |
| 2003/0023295 A1 * | 1/2003 | Osypka | 607/122 |
| 2003/0028232 A1 | 2/2003 | Camps et al. | |
| 2003/0045919 A1 | 3/2003 | Swoyer et al. | |
| 2003/0055463 A1 | 3/2003 | Gordon et al. | |
| 2003/0125787 A1 | 7/2003 | Shchervinsky | |
| 2003/0204231 A1 | 10/2003 | Hine et al. | |
| 2004/0010282 A1 | 1/2004 | Kusleika | |
| 2004/0015193 A1 * | 1/2004 | Lamson et al. | 607/9 |
| 2004/0054388 A1 | 3/2004 | Osypka | |
| 2004/0260371 A1 | 12/2004 | Greenland et al. | |
| 2005/0033394 A1 | 2/2005 | Seifert et al. | |
| 2005/0033395 A1 | 2/2005 | Seifert et al | |
| 2005/0033396 A1 | 2/2005 | Osypka | |
| 2005/0070986 A1 | 3/2005 | Tockman et al. | |

FOREIGN PATENT DOCUMENTS

| | | |
|---|---|---|
| DE | 4425195 | 4/2003 |
| EP | 1000634 | 5/2000 |
| EP | 1025802 A | 8/2000 |
| GB | 2025236 A | 1/1980 |
| WO | 2004091716 | 10/2004 |
| WO | 2004028023 | 3/2005 |

OTHER PUBLICATIONS

Epstein et al., Long-Term Performance of Bipolar Epicardial Atrial Pacing Using an Active Fixation Bipolar Endocardial Lead, PACE, Apr. 1998.

Karpawich et al., Improved Eplmyocardial Pacing, PACE, Nov. 1994.

Worley et al., Construction of a Multipolar Electrode System Referenced and Anchored to Endocardium for Study of Arrhythmias, American Physiological Society, 1986.

Office Action recieved in related case U.S. Appl. No. 10/972,298, mailed Apr. 17, 2007.

Office Action received in related case U.S. Appl. No. 10/972,049, mailed Jul. 24, 2006.

Office Action received in related case U.S. Appl. No. 10/972,049, mailed Jan. 11, 2007.

Office Action received in related case U.S. Appl. No. 10/821,421, mailed May 25, 2006.

Office Action received in related case U.S. Appl. No. 10/821,421, mailed Nov. 24, 2006.

Office Action received in related case U.S. Appl. No. 10/821,421, mailed Mar. 22, 2007.

German Office Action citing prior art to related German Patent Application and English translation thereof.

International Search Report and Written Opinion of International Application No. PCT/2004/010907, filed Apr. 9, 2004, both mailed Sep. 16, 2004.

International Search Report and Written Opinion of International Application No. PCT/US2004/035172, filed Oct. 22, 2004, both mailed Jan. 31, 2005.

Office Action received in related case U.S. Appl. No. 10/971,577, mailed Aug. 7, 2007.

Office Action received in related case U.S. Appl. No. 10/972,049, mailed Jul. 2, 2007.

Agreement between Cardiac Pacemakers, Inc. and Dr. Osypka GmbH, dated Aug. 26, 2002, 2 pp.

* cited by examiner

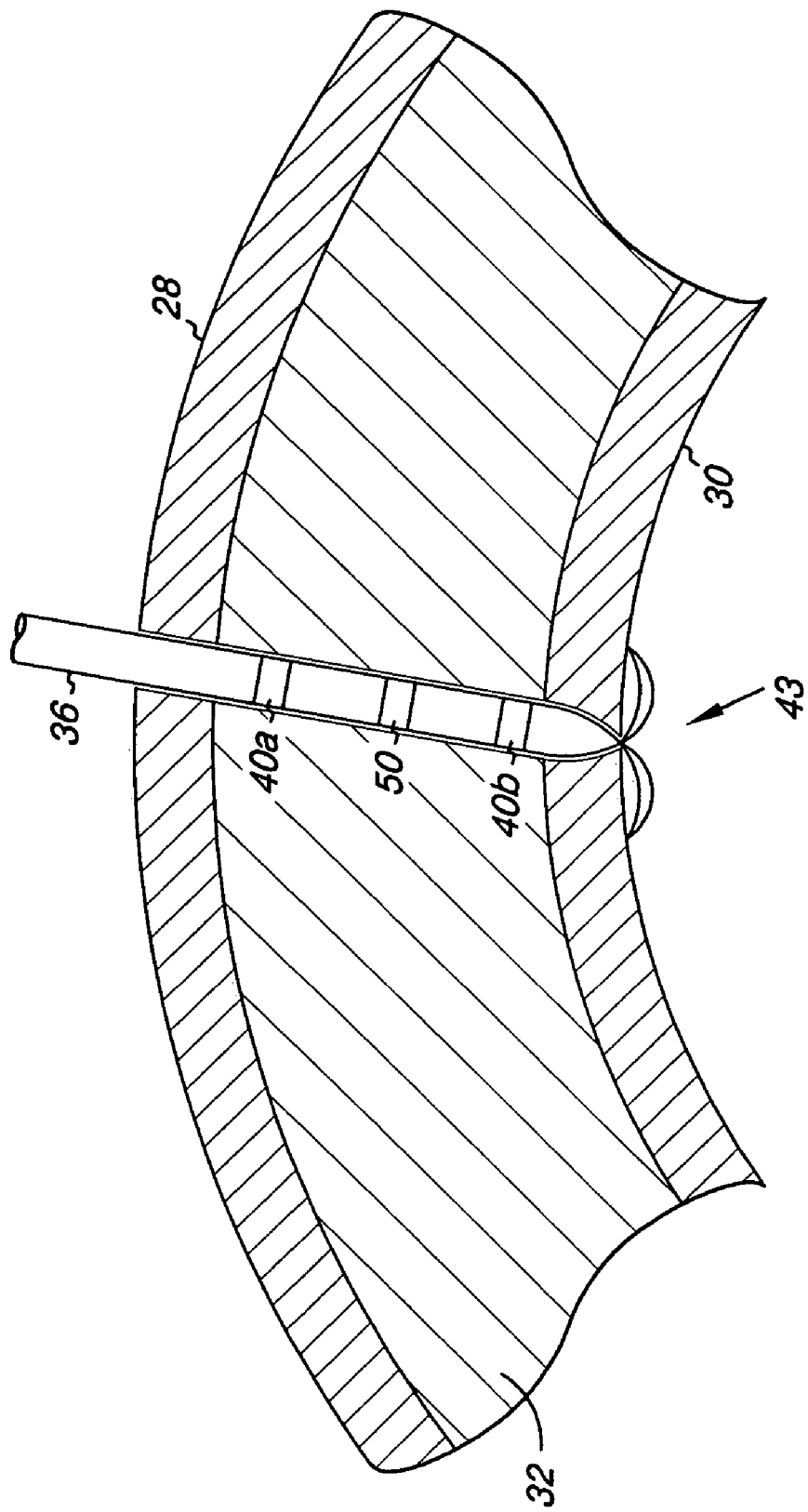

MYOCARDIAL LEAD WITH FIXATION MECHANISM

CROSS REFERENCES

The present application claims the benefit of the following U.S. Provisional Application: Application Ser. No. 60/514,037 filed Oct. 24, 2003, entitled "Absorbable Myocardial Lead Fixation System", Application Ser. No. 60/514,665 filed Oct. 27, 2003, entitled "Lead Electrode Arrangement for Myocardial Leads", Application Ser. No. 60/514,042 filed Oct. 24, 2003, entitled "Tapered Tip for Myocardial Lead", Application Ser. No. 60/514,714 filed Oct. 27, 2003, entitled "Minimally-Invasive Fixation Systems for Over-the-Tether Myocardial Leads", Application Ser. No. 60/514,039 filed Oct. 24, 2003, entitled "Distal or Proximal Fixation of Over-the-Suture Myocardial Leads", Application Ser. No. 60/514,146 filed Oct. 24, 2003, entitled "Myocardial Lead with Fixation Mechanism", Application Ser. No. 60/514,038 filed Oct. 24, 2003 entitled "Delivery Instrument for Myocardial Lead Placement" and Application Ser. No. 60/514,713 filed Oct. 27, 2003, entitled "Drug-Eluting Myocardial Leads", all of which are incorporated herein by reference.

Reference is hereby made to the following commonly assigned U.S. Patent Application Ser. No. 10/821,421, filed Apr. 9, 2004 entitled "Cardiac Electrode Anchoring System" and the following commonly assigned U.S. Patent Applications filed on an even date herewith, all of which are incorporated herein by reference: Application Ser. No. 10/972,049, entitled "Myocardial Lead", Application Ser. No. 10/972,298, entitled "Distal or Proximal Fixation of Over-the-Tether Myocardial Leads", Application Ser. No. 10/971 577, entitled "Absorbable Myocardial Lead Fixation System" and Application Ser. No. 10/971,551, entitled "Myocardial Lead Attachment System."

PARTIES TO A JOINT RESEARCH AGREEMENT

The claimed invention was made subject to a joint research agreement between Cardiac Pacemakers, Inc. and Dr. Osypka, GmbH.

FIELD OF THE INVENTION

This invention relates generally to implantable lead assemblies for stimulating and/or sensing electrical signals in muscle tissue. More particularly, it relates to myocardially-implanted leads for cardiac stimulation and systems for anchoring the leads.

BACKGROUND OF THE INVENTION

Cardiac rhythm management systems are used to treat heart arrhythmias. Pacemaker systems are commonly implanted in patients to treat bradycardia (i.e., abnormally slow heart rate). A pacemaker system includes an implantable pulse generator and leads, which form the electrical connection between the implantable pulse generator and the heart. An implantable cardioverter defibrillator ("ICD") is used to treat tachycardia (i.e., abnormally rapid heart rate). An ICD also includes a pulse generator and leads that deliver electrical energy to the heart.

The leads coupling the pulse generator to the cardiac muscle are commonly used for delivering an electrical pulse to the cardiac muscle, for sensing electrical signals produced in the cardiac muscle, or for both delivering and sensing. The leads are susceptible to categorization according to the type of connection they form with the heart. An endocardial lead includes at least one electrode at or near its distal tip adapted to contact the endocardium (i.e., the tissue lining the inside of the heart). An epicardial lead includes at least one electrode at or near its distal tip adapted to contact the epicardium (i.e., the tissue lining the outside of the heart). Finally, a myocardial lead includes at least one electrode at or near its distal tip inserted into the heart muscle or myocardium (i.e., the muscle sandwiched between the endocardium and epicardium). Some leads have multiple spaced apart distal electrodes at differing polarities and are known as bipolar type leads. The spacing between the electrodes can affect lead performance and the quality of the electrical signal transmitted or sensed through the heart tissue.

The lead typically consists of a flexible conductor surrounded by an insulating tube or sheath that extends from the electrode at the distal end to a connector pin at the proximal end. Endocardial leads are typically delivered transvenously to the right atrium or ventricle and commonly employ tines at a distal end for engaging the trabeculae.

The treatment of congestive heart failure ("CHF"), however, often requires left ventricular stimulation either alone or in conjunction with right ventricular stimulation. For example, cardiac resynchronization therapy ("CRT") (also commonly referred to as biventricular pacing) is an emerging treatment for heart failure, which requires stimulation of both the right and the left ventricle to increase cardiac output. Left ventricular stimulation requires placement of a lead in or on the left ventricle near the apex of the heart. One technique for left ventricular lead placement is to expose the heart by way of a thoracotomy. The lead is then positioned so that the electrodes contact the epicardium or are embedded in the myocardium. Another method is to advance an epicardial lead endovenously into the coronary sinus and then advance the lead through a lateral vein of the left ventricle. The electrodes are positioned to contact the epicardial surface of the left ventricle.

The left ventricle beats forcefully as it pumps oxygenated blood throughout the body. Repetitive beating of the heart, in combination with patient movement, can sometimes dislodge the lead from the myocardium. The electrodes may lose contact with the heart muscle, or spacing between electrodes may alter over time.

There is a need for an improved myocardial lead and attachment system suitable for chronic implantation.

SUMMARY OF THE INVENTION

According to one embodiment, the present invention is a myocardial lead attachment system for securing a distal end of a lead within the myocardium of a patient's heart. The system includes an anchor, a tether coupled at a distal end to the anchor and a lead body. The lead body has a proximal end, a distal end, and a lumen extending therethrough for receiving the tether. The system further includes a fixation mechanism at the distal end of the lead body. The fixation mechanism is adapted to collapse to a first configuration during implantation and deploy to a second configuration after implantation.

According to another embodiment, the present invention is a method of implanting a myocardial lead attachment system of the type including a lead body, an anchor, a tether and a fixation mechanism. The lead body and fixation mechanism are advanced through the heart while the fixation mechanism is in a first collapsed configuration. The fixation mechanism is deployed to a second configuration to retain the lead body at a chosen location.

This summary is not intended to describe each embodiment or every implementation of the present invention. Advantages and a more complete understanding of the invention will become apparent upon review of the detailed description and claims in conjunction with the accompanying drawings.

BRIEF DESCRIPTION OF THE DRAWINGS

FIG. 7B is a partial sectional view of portion of the vasculature schematically illustrating a myocardial lead attachment system in an epicardial-endocardial configuration.

Figure 1:
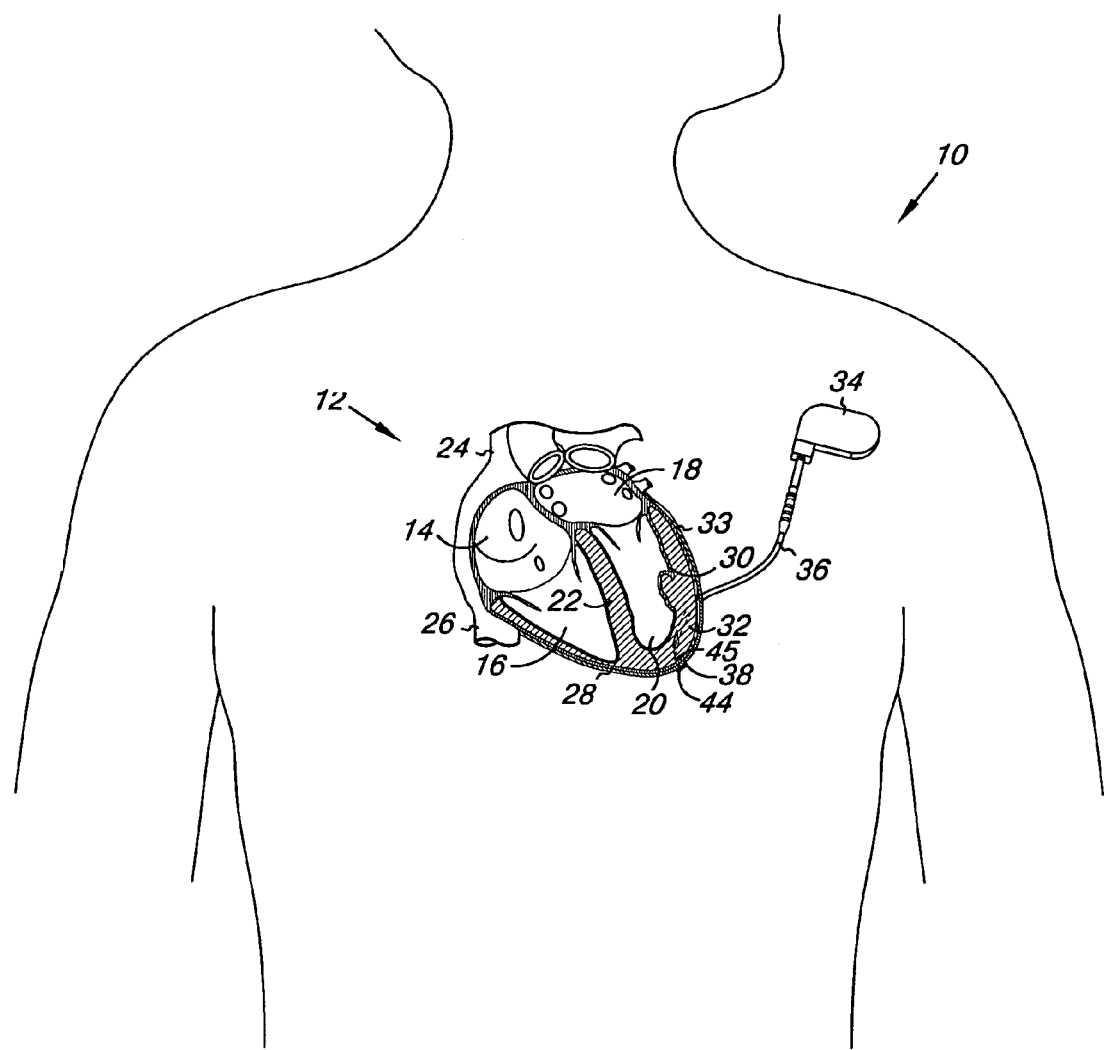
FIG. 1 is a sectional view of a portion of the vasculature showing a myocardial lead attachment and pacing system according to one embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view of a myocardial lead attachment and pacing system 10 deployed in a human heart 12 according to one embodiment of the present invention. As shown in FIG. 1, the heart 12 includes a right atrium 14 and a right ventricle 16 separated from a left atrium 18 and a left ventricle 20 by a septum 22. During normal operation of the heart 12, deoxygenated blood is fed into the right atrium 14 through the superior vena cava 24 and the inferior vena cava 26. The deoxygenated blood flows from the right atrium 14 into the right ventricle 16. The deoxygenated blood is pumped from the right ventricle 16 into the lungs, where the blood is re-oxygenated. From the lungs the oxygenated blood flows into the left atrium 18, then into the left ventricle 20. The left ventricle 20 beats forcefully to pump the oxygenated blood throughout the body.

The outer walls of the heart 12 are lined with a tissue known as the epicardium 28. The inner walls of the heart are lined with a tissue known as the endocardium 30. The heart muscle, or myocardium 32, is sandwiched between the endocardium 30 and the epicardium 28. An outer pericardial sac 33 surrounds the heart 12.

The attachment and pacing system 10 includes a pulse generator 34 coupled to a myocardial lead 36. The pulse generator 34 is typically implanted in a pocket formed underneath the skin of the patient's chest or abdominal region. The lead 36 extends from the pulse generator 34 to the heart 12 and is implanted in the myocardium 32 near an apex 38 of the heart 12. The lead 36 delivers electrical signals from the pulse generator 34 to an electrode positioned on the lead 36 (not visible in FIG. 1) to accomplish pacing of the heart 12. The myocardial lead 36 is further provided with a fixation mechanism 43 to secure the lead 36 within the heart 12 following implantation.

The lead 36 is shown coupled to an anchor mechanism 44 and a tether 45. Placement of the lead 36 and anchor mechanism 44 in the heart 12 may be accomplished by exposing a portion of the heart 12, for example, by way of a thoracotomy or mini-thoracotomy. According to other embodiments, the heart 12 may be accessed via an endoscopic procedure according to known methods. The lead 36 and anchor mechanism 44 are positioned in the heart 12 with the assistance of a delivery instrument. Suitable delivery instruments and methods of implanting the anchor mechanism 44 and lead 36 are described in the above-identified application "Myocardial Lead Attachment System".

Figure 2:
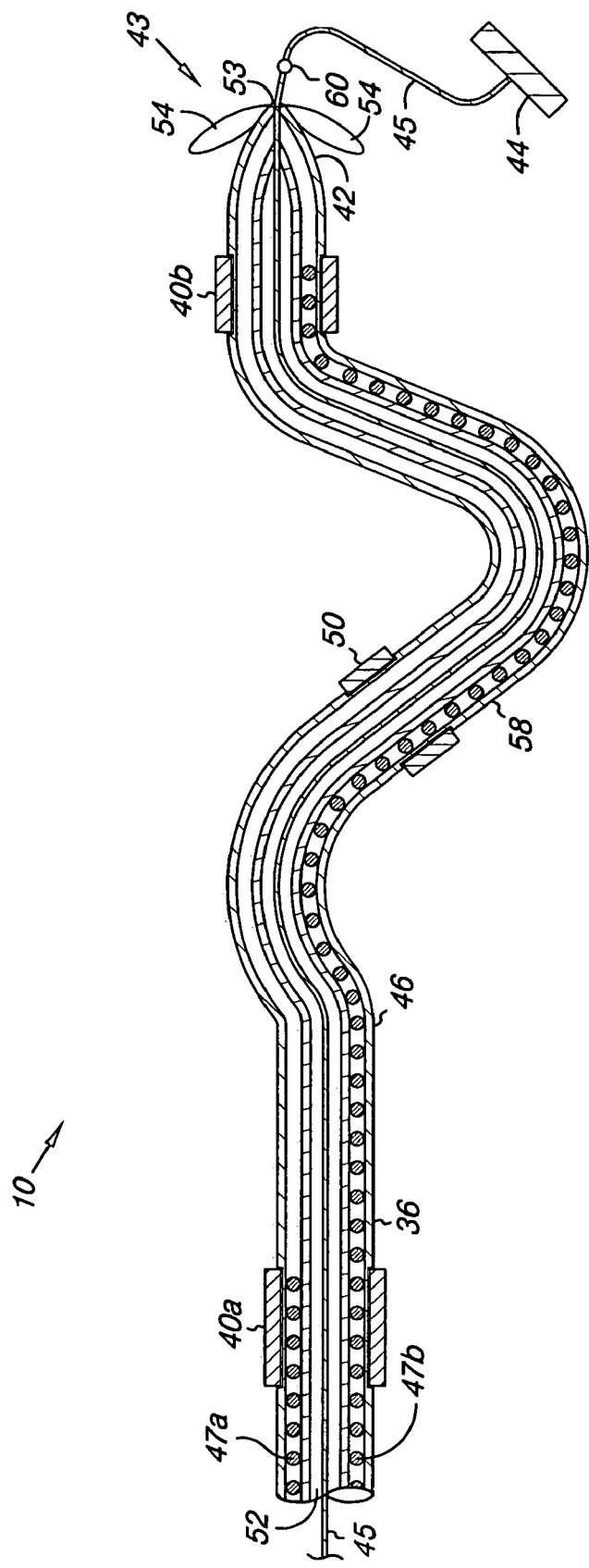
FIG. 2 is a side sectional view of a distal portion of the myocardial lead attachment and pacing system of FIG. 1.

FIG. 2 shows an more detailed sectional view of a distal portion of the attachment system 10 of FIG. 1. The lead 36 includes one or more proximal electrodes 40a positioned proximal to one or more distal electrodes 40b located near a distal tip 42 of the lead 36. A pair of coiled conductive members 47a and 47b are coupled to the proximal electrode 40a and the distal electrode 40b, respectively, and are protected by an outer insulating sheath 46. The lead 36 further includes one or more drug collars 50 for releasing therapeutic agents following implantation. According to other embodiments, the lead 102 does not include the drug collar 50. The lead 36 also includes a lumen 52 extending therethrough for receiving the tether 45.

The fixation mechanism 43 is positioned at the distal tip 42 of the lead 36. The fixation mechanism 43 includes a through-hole 53 to receive the tether 45, which also extends through the lead lumen 52. The fixation mechanism 43 is formed of a plurality of tines or fins 54 extending outwardly from the lead 36. In a first configuration (not shown), the tines 54 are collapsed against the lead 36 to facilitate advancement of the lead 36 through the heart 12. In a second configuration, illustrated in FIG. 2, the tines 54 extend radially outwardly from the lead 36 and resist movement of the lead 36 through the heart 12. Generally, the fixation mechanism 43 has a first diameter in the first configuration and a second diameter in the second configuration greater than the first diameter. According to other embodiments (not shown), the fixation mechanism 43 is positioned on the lead 36 proximal to the distal tip 42.

In one embodiment, a distally directed axial force drawing or pushing the lead 36 forward or in a distal direction through the myocardium 32 retains the fixation mechanism 43 in the first configuration. Likewise, a proximally directed force pulling the lead 36 back or in a proximal direction deploys the fixation mechanism 43 in the second configuration. In another embodiment, movement through the myocardium 32 in a distal direction collapses the fixation mechanism 43 while movement through the myocardium 32 in a proximal direction frictionally engages the fixation mechanism 43, deploying it to the second configuration. In other embodiments, rotating the fixation mechanism 43 in a first direction retains the fixation mechanism 43 in the first configuration and rotating or pulling the fixation mechanism 43 in a second direction deploys the fixation mechanism 43 into the second configuration.

The lead 36 includes a bias region 58 proximal to the fixation mechanism 43. Bias region 58 is a two or three-dimensional feature formed by a curvature of the lead 36. The bias region 58 absorbs axial loading at a proximal end 35 of the lead 36 without translating it into motion at the distal tip 42. This reduces intra-myocardial electrode motion and strain on the fixation mechanism 0.43 and distal migration of the lead 36. The proximal electrode 40a is positioned proximal to the bias region 58 and the distal electrode 40b is positioned distal to the bias region 58. In other embodiments, the electrodes 40a and 40b are both positioned proximal or distal to the bias region 58. In another embodiment (not shown), the lead 36 does not include the bias region 58.

A lock 60 is formed on the tether 45 and is receivable in a lock housing formed on the lead 36 to produce a locking arrangement (not shown). Suitable lock arrangements are described in the above-identified application "Distal or Proximal Fixation of Over-the-Tether Myocardial Leads". The through-hole 53 in the fixation mechanism 43 is sized to receive and pass over the lock 60.

According to one embodiment, either or both of the anchor mechanism 44 and tether 45 are dissolvable. Suitable dissolvable anchor mechanisms and tethers are described in the above-identified "Absorbable Myocardial Lead Fixation System". Following dissolution of either or both of the anchor mechanism 44 and the tether 45, the fixation mechanism 43 provides stability to the implanted lead 102.

Figure 3:
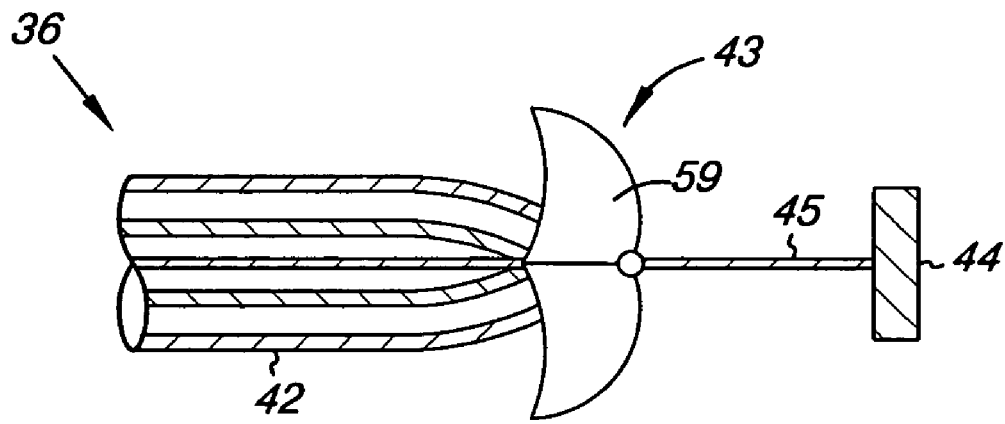
FIG. 3 is a side sectional view of the fixation mechanism shown in FIG. 2 according to another embodiment of the present invention.

FIG. 3 shows another embodiment of the fixation mechanism 43, in which the fixation mechanism 43 is shaped as a ribbed tent or umbrella 59. In the first configuration (not shown), the umbrella 59 is deflated and collapsed against the lead 36. In the second configuration, illustrated in FIG. 3, the umbrella 59 is inflated and expanded radially outward. In still other embodiments (not shown), the fixation mechanism 43 is shaped like a disc or bar or other shape chosen to advance easily through the heart 12 in a first configuration and engage the heart 12 in a second configuration to the secure the lead 36 in place.

Figure 4:
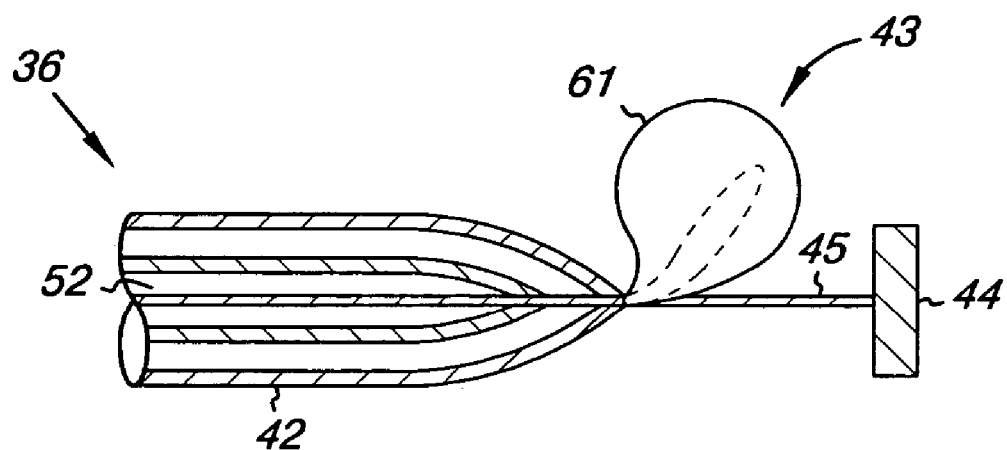
FIG. 4 is a side sectional view of the fixation mechanism shown in FIG. 2 according to another embodiment of the present invention.

FIG. 4 shows another embodiment of the fixation mechanism 43, in which the fixation mechanism 43 is an inflatable balloon 61. In the first configuration, shown in dotted lines, the balloon 61 is deflated. In the second configuration, the balloon 61 is inflated so as to have a greater diameter than in the first configuration. The balloon 61 may be inflatable via fluids, including air, water or other fluids or gases. Such balloon deployment fluids are carried to the balloon 61 through the lead lumen 52. While shown superimposed over the tether 45, the balloon 61 would reside to the side of the tether 45.

Figure 5A:
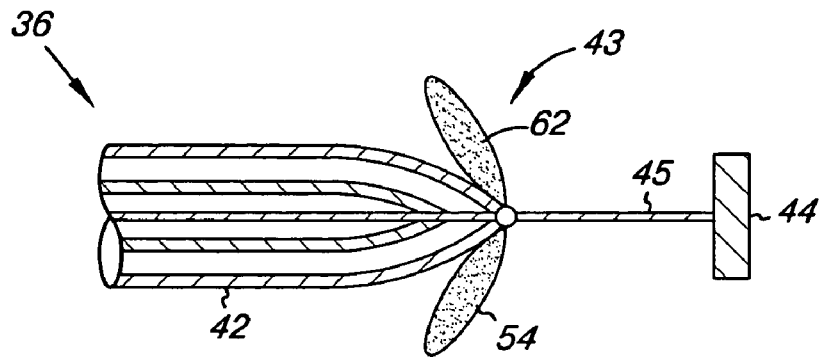
FIG. 5A is a side sectional view of the fixation mechanism shown in FIG. 2 including a surface feature according to another embodiment of the present invention.

FIG. 5A shows another embodiment of the fixation mechanism 43 in which the fixation, mechanism 43 is provided with a roughened or porous surface feature, 62. Surface feature 62 promotes the ingrowth of collagenous encapsulation tissue ("scar tissue") following implantation of the lead 36. Suitable surface features are described in the above-identified application "Absorbable Myocardial Lead Fixation System". Surface feature 62 is conducive to cellular attachment as described to enhance long term fixation of the lead 36 within the heart 12.

Figure 5B:
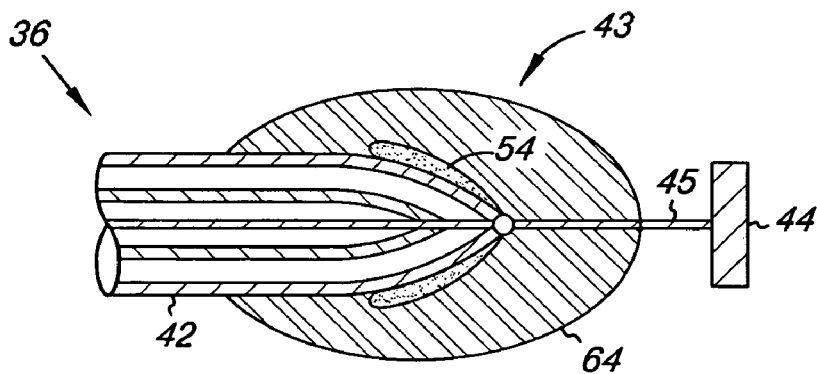
FIG. 5B is a side sectional view of the fixation mechanism of FIG. 5A including a dissolvable coating according to one embodiment of the present invention.

According to one embodiment, as shown in FIG. 5B, a rapidly dissolvable coating 64 is formed over the fixation mechanism 43. The coating 64 may be water soluble. Suitable rapidly dissolvable coatings are described in the above-identified applications "Absorbable Myocardial Lead Fixation System" and "Myocardial Lead". The coating 64 masks the surface feature 62, reducing friction between the surface feature 62 and the heart 12, facilitating passage of the fixation mechanism 43 through the heart 12.

The coating 64 masks the shape of the fixation mechanism 43 as well as the surface feature 62. The coating 64 retains the fixation mechanism 43 in the first configuration until the coating 64 dissolves, preventing premature deployment of the fixation mechanism 43 to the second configuration. Following dissolution, the fixation mechanism 43 may be deployed to the second configuration and the surface feature 62 is revealed to permit tissue ingrowth.

Figure 5C:
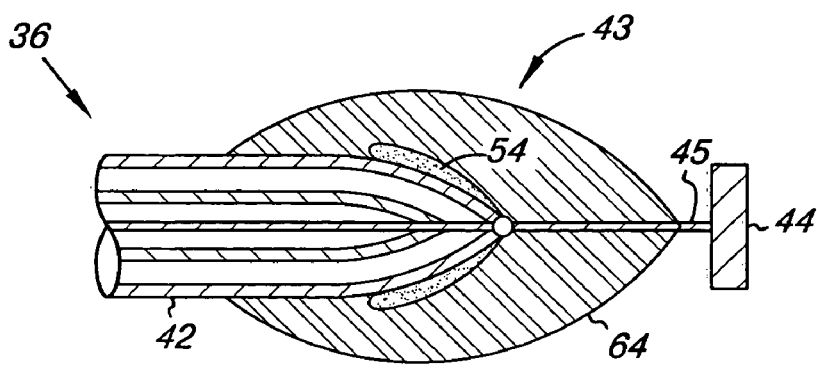
FIG. 5C is a side sectional view of the fixation mechanism of FIG. 5A including a dissolvable coating according to another embodiment of the present invention.

According to one embodiment, the coating 64 forms a first implant friendly shape around the fixation mechanism 43. The implant friendly shape may be rounded or have a blunt leading edge and is chosen to reduce trauma to the myocardial tissue 32 during insertion. According to still another embodiment, shown in FIG. 5C, the coating 64 forms a more pointed shape chosen to facilitate dissection or dilation of the myocardium 32 during insertion.

Figure 6:
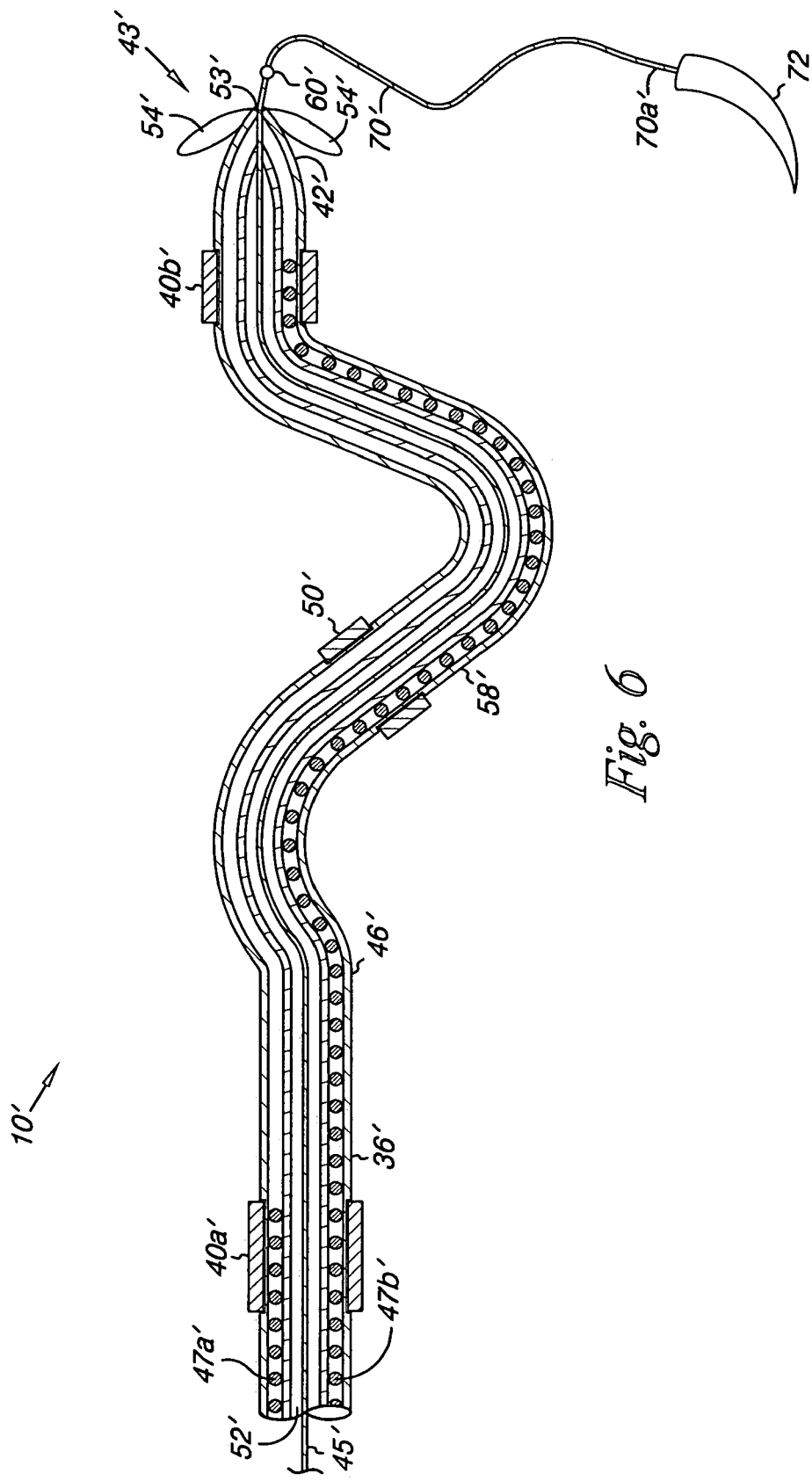
FIG. 6 is a side sectional view of a distal portion of a myocardial lead attachment system according to another embodiment of the present invention.

FIG. 6 shows a distal portion of a myocardial lead attachment and pacing system 10' according to another embodiment of the present invention. System 10' is generally similar to system 10 of FIG. 2 and includes many of the same features. Contrary to the embodiment shown in FIG. 2, myocardial lead attachment system 10' is adapted to be inserted into the heart 12 without the use of a delivery instrument as previously described. According to the embodiment shown in FIG. 6, the myocardial lead 36' is coupled to a pull-through type suture 70', which is coupled at a distal end 70a' to a needle 72'. The needle 72' is used to penetrate the epicardial surface 28 and is advanced through the myocardium 32. The lead 36' is pulled behind the needle 72' through the heart 12 with the pull-through suture 70'. The fixation mechanism 43' is retained in a first configuration as the lead 36' is advanced through the heart 12. When the distal tip 42' of the lead 36' has reached a chosen implant site, the fixation mechanism 43' is deployed to a second configuration to secure the lead 36' in place. The suture 70' and needle 72' are then cut from the lead 36 and removed.

Figure 7A:
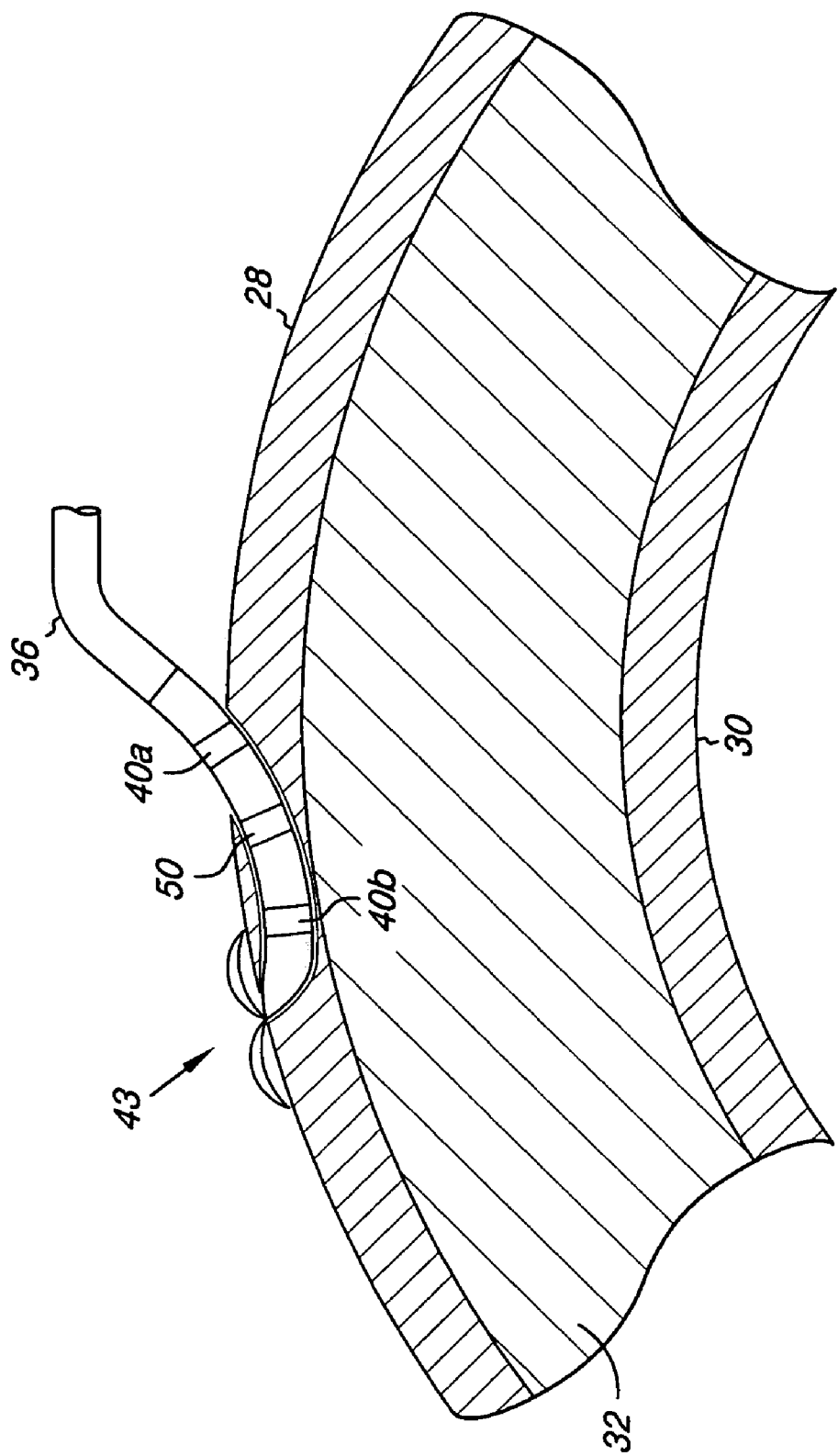
FIG. 7A is a partial sectional view of portion of the vasculature schematically illustrating a myocardial lead attachment system in an epicardial-epicardial configuration.
Figure 7C:
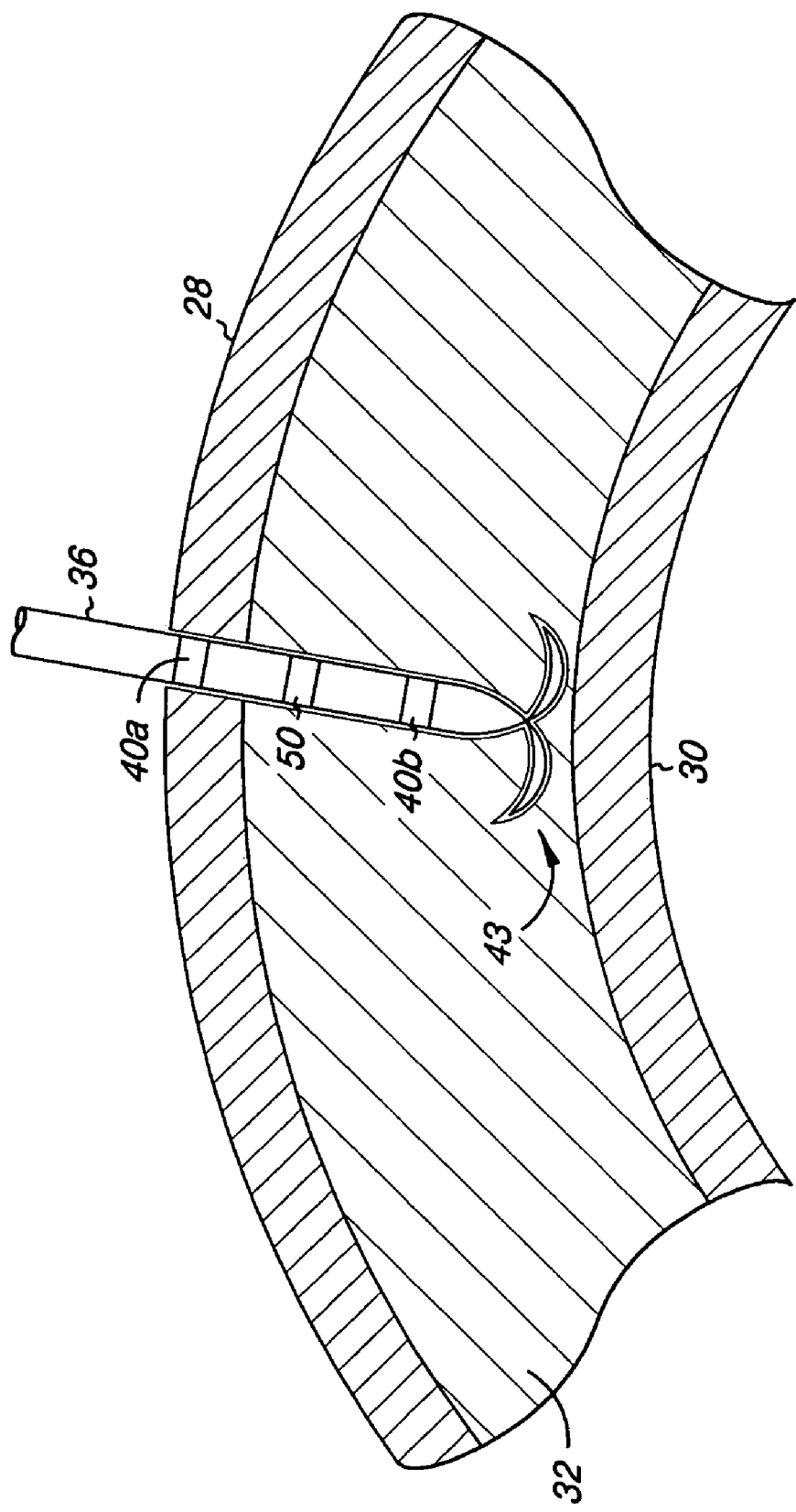
FIG. 7C is a partial sectional view of portion of the vasculature schematically illustrating a myocardial lead attachment system in an intramyocardial configuration.
Figure 7D:
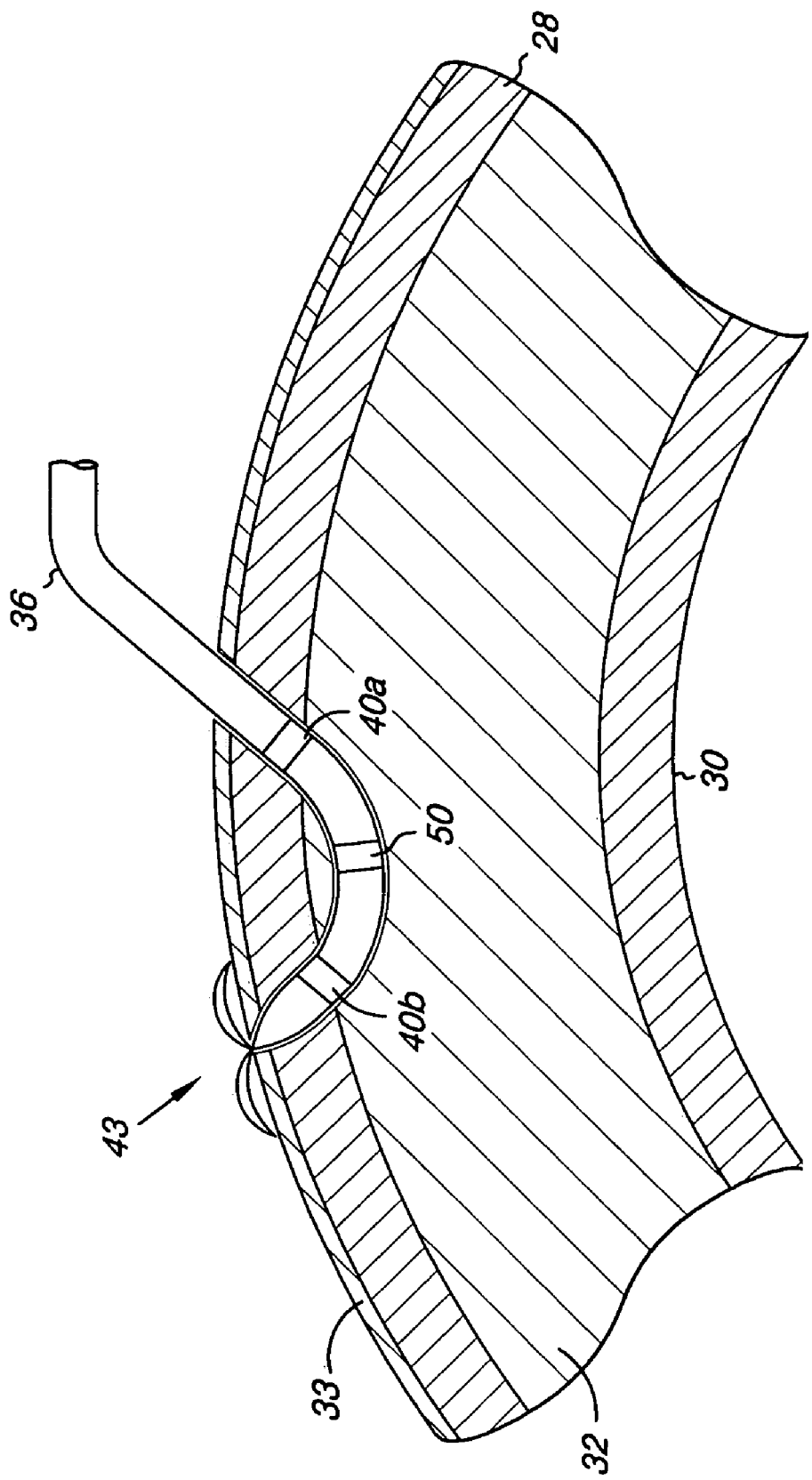
FIG. 7D is a partial sectional view of portion of the vasculature schematically illustrating a myocardial lead attachment system in a pericardial-pericardial configuration.

FIGS. 7A-7D shows sectional views of a portion of the vasculature and a distal portion of the myocardial lead attachment system 10 of FIG. 2 with the fixation mechanism 43 deployed in the heart 12 in various lead configurations. The fixation mechanism 43 may be deployed on a surface of the epicardium 28 (FIG. 7A), the endocardium 30 (FIG. 7B), within the myocardium 32 (FIG. 7C), or on the surface of the pericardium 33 (FIG. 7D). The fixation mechanism 43 resists proximally directed axial forces exerted on the lead 36. The lead 36 is advantageously stabilized and intra-myocardial motion and migrations are reduced. While generally showing the system 10 of FIG. 2, the system 10' of FIG. 6 may also be deployed as shown.

Various modifications and additions can be made to the exemplary embodiments discussed without departing from the scope of the present invention. Accordingly, the scope of the present invention is intended to embrace all such alternatives, modifications, and variations as fall within the scope of the claims, together with all equivalents thereof.

The invention claimed is:

1. A method of implanting a myocardial lead attachment system, the method comprising:
   delivering an anchor mechanism coupled to a distal end of a tether to an epicardial surface;
   threading a lead body having a proximal end, a distal end, a lumen extending through the lead body, and a fixation mechanism positioned at the distal end over a proximal end of the tether;
   advancing the lead body and fixation mechanism over the tether toward the anchor and through the myocardium while the fixation mechanism is in a first collapsed configuration; and
   deploying the fixation mechanism to a second configuration on the epicardial surface of the heart to retain the lead body at a chosen location.

2. The method of claim 1 wherein deploying the fixation mechanism includes exerting a proximally directed axial force on the lead body.

3. The method of claim 1 wherein the method further includes:
   rotating the fixation mechanism in a first direction to retain the fixation mechanism in the first configuration; and
   deploying the fixation mechanism further includes rotating the fixation mechanism in a second direction.

4. The method of claim 1 wherein deploying the fixation mechanism further includes inflating the fixation mechanism with a deployment fluid.

5. The method of claim 1 wherein the method further comprises allowing a rapidly dissolvable coating on the fixation mechanism to dissolve before deploying the fixation mechanism to the second configuration.

6. The method of claim 1 wherein the method further includes fixing the fixation mechanism to the heart through cellular attachment.

7. The method of claim 1 further comprising allowing the anchor mechanism or the tether to dissolve.

8. The method of claim 1 wherein the method further includes:
   coupling a proximal end of a pull-through type tether to the lead body and a distal end of the tether to a needle;
   advancing the needle through the heart; and
   advancing the lead further includes pulling the lead body behind the needle with the tether.

9. The method of claim 1 wherein the method further includes:
   coupling the proximal end of the lead body to a pulse generator; and
   delivering electrical signals from the pulse generator to an electrode positioned on the lead body.

10. A method of implanting a myocardial lead attachment system, the method comprising:
    delivering an anchor mechanism coupled to a distal end of a tether to an epicardial surface;
    threading a lead body having a proximal end, a distal end, a lumen extending through the lead body, and a fixation mechanism positioned at the distal end over a proximal end of the tether;
    advancing the lead body and fixation mechanism over the tether toward the anchor and through the myocardium while the fixation mechanism is in a first collapsed configuration;
    deploying the fixation mechanism to a second configuration on the epicardial surface of the heart to retain the lead body at a chosen location; and
    coupling the lead body to the anchor mechanism and the tether.

11. The method of claim 10 wherein deploying the fixation mechanism includes exerting a proximally directed axial force on the lead body.

12. The method of claim 10 wherein the method further includes:
    rotating the fixation mechanism in a first direction to retain the fixation mechanism in the first configuration; and
    deploying the fixation mechanism further includes rotating the fixation mechanism in a second direction.

13. The method of claim 10 wherein deploying the fixation mechanism further includes inflating the fixation mechanism with a deployment fluid.

14. The method of claim 10 wherein the method further comprises allowing a rapidly dissolvable coating on the fixation mechanism to dissolve before deploying the fixation mechanism to the second configuration.

15. The method of claim 10 wherein the method further includes fixing the fixation mechanism to the heart through cellular attachment.

16. The method of claim 10 further comprising allowing the anchor mechanism or the tether to dissolve.

17. The method of claim 10 wherein the method further includes:
    coupling a proximal end of a pull-through type tether to the lead body and a distal end of the tether to a needle;
    advancing the needle through the heart; and
    advancing the lead further includes pulling the lead body behind the needle with the tether.

18. The method of claim 10 wherein the method further includes:
    coupling the proximal end of the lead body to a pulse generator and
    delivering electrical signals from the generator to an electrode positioned on the lead body.

* * * * *

UNITED STATES PATENT AND TRADEMARK OFFICE
CERTIFICATE OF CORRECTION

PATENT NO. : 7,418,298 B2
APPLICATION NO. : 10/971549
DATED : August 26, 2008
INVENTOR(S) : Jason A. Shiroff et al.

Page 1 of 1

It is certified that error appears in the above-identified patent and that said Letters Patent is hereby corrected as shown below:

<u>On the title page, Item (56) References Cited, U.S. Patent Documents</u>
3,244,174 A  4/1966    delete "Wexbey" and replace it with  -- Wesbey --

<u>On the title page, page 2, Item (56) References Cited, Other Publications</u>
Karpawich et al. (1194)  delete "Eplmyocardial" and replace it with -- Epimyocardial --

<u>Column 8, line 48</u>
Insert a semi-colon after the word "generator"

Signed and Sealed this

Seventeenth Day of February, 2009

JOHN DOLL
*Acting Director of the United States Patent and Trademark Office*